United States Patent [19]

Blum et al.

[11] 4,064,164
[45] Dec. 20, 1977

[54] 1,3-DI-AMINO-ALKANE-1,1-DIPHOSPHONIC ACIDS AND SALTS

[75] Inventors: Helmut Blum; Karl-Heinz Worms, both of Dusseldorf, Germany

[73] Assignee: Henkel Kommanditgesellschaft auf Aktien, Dusseldorf-Holthausen, Germany

[21] Appl. No.: 705,793

[22] Filed: July 16, 1976

[30] Foreign Application Priority Data

Aug. 1, 1975 Germany .............................. 2534390

[51] Int. Cl.² .......................... C07F 9/38; C02B 5/06; A61K 7/22
[52] U.S. Cl. .................................. 260/502.5; 210/58; 252/8.8; 252/180; 252/545; 260/501.12; 424/54; 424/204
[58] Field of Search ...................................... 260/502.5

[56] References Cited

U.S. PATENT DOCUMENTS

| | | | |
|---|---|---|---|
| 3,398,127 | 8/1968 | Suling et al. ....................... | 260/502.5 |
| 3,919,296 | 11/1975 | Schindler et al. .................. | 260/502.5 |
| 3,925,456 | 12/1975 | Ploger et al. ....................... | 260/502.5 |
| 3,976,762 | 8/1976 | Kohler et al. ...................... | 260/502.5 |
| 4,005,160 | 1/1977 | Redmore et al. .................. | 260/502.5 |

FOREIGN PATENT DOCUMENTS

| | | | |
|---|---|---|---|
| 1,002,355 | 2/1957 | Germany .......................... | 260/502.5 |
| 995,462 | 6/1965 | United Kingdom .............. | 260/502.5 |

*Primary Examiner*—Joseph E. Evans
*Attorney, Agent, or Firm*—Hammond & Littell

[57] ABSTRACT

1,3-Di-amino-alkane-1,1-diphosphonic acids having the formula

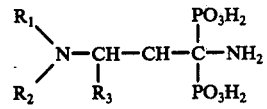

wherein $R_1$ and $R_2$ are members selected from the group consisting of hydrogen and alkyl having 1 to 3 carbon atoms, and $R_3$ is a member selected from the group consisting of hydrogen and methyl; as well as their water-soluble salts. The 1,3-diamino-alkane-1,1-diphosphonic acids are excellent sequestering agents especially for alkaline earth metal ions. The compounds are useful in pharmaceutical preparations for treatment of disturbances of calcium or phosphate metabolism or cosmetic preparations such as toothpastes or mouth washes for the prevention of tartar and plaque depositions.

7 Claims, No Drawings

1,3-DI-AMINO-ALKANE-1,1-DIPHOSPHONIC ACIDS AND SALTS

RELATED ART

Certain diphosphonic acids, for example, hydroxyethane-diphosphonic acid and aminoethane-diphosphonic acid are known to be good complex-forming substances, which may also be used in less than stoichiometric amounts. Compared with the polyphosphates, which are also in less than the stoichiometric amounts, they have the advantage of being stable to hydrolysis. In addition, 1-hydroxy-3-aminopropane-1,1-diphosphonic acid has also been proposed as a particularly suitable complex-forming compound (German Published Specification DOS 2,130,794).

OBJECTS OF THE INVENTION

An object of the present invention is the obtaining of a 1,3-di-amino-alkane-1,1-diphosphonic acid compound of the formula

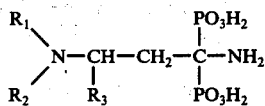

wherein $R_1$ and $R_2$ are members selected from the group consisting of hydrogen and alkyl having from 1 to 3 carbon atoms and $R_3$ is a member selected from the group consisting of hydrogen and methyl and a nontoxic, pharmaceutically acceptable water-soluble salt thereof.

Another object of the present invention is the development of a process for the production of the above 1,3-di-amino-alkane-1,1-diphosphonic acids or their water-soluble salts.

A further object of the present invention is the development of a process for the delaying or inhibiting of the precipitation of alkaline earth metal ions from solution by the use of stoichiometric to substoichiometric amounts of the above 1,3-di-amino-alkane-1,1-diphosphonic acids or their water-soluble salts.

A yet further object of the present invention is the development of a method for the treatment of diseases related to the abnormal deposition or dissolution of difficultly soluble calcium salts which comprises administering a safe but effective amount of at least one of the above 1,3-di-amino-alkane-1,1-diphosphonic acids or their water-soluble salts to the warm blooded animal.

These and other objects of the invention will become more apparent as the description thereof proceeds.

DESCRIPTION OF THE INVENTION

The above objects have been achieved by the development of new 1,3-di-amino-alkane-1,1-diphosphonic acid derivatives which are similar in their structure to 1-hydroxy-3-amino-propane-1,1-diphosphonic acids, but have considerably better properties.

The new 1,3-di-alkane-1,1-diphosphonic acids correspond to the formula I:

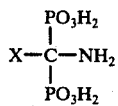

(I)

in which

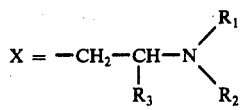

and $R_1$ and $R_2$ represent a hydrogen atom or an alkyl radical having 1 to 3 carbon atoms, and $R_3$ represents a hydrogen atom or a methyl radical.

More particularly, the new compounds of the invention are a 1,3-diamino-alkane-1,1-diphosphonic acid compound of the formula

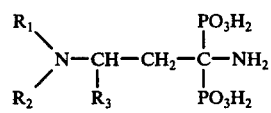

wherein $R_1$ and $R_2$ are members selected from the group consisting of hydrogen and alkyl having from 1 to 3 carbon atoms and $R_3$ is a member selected from the group consisting of hydrogen and methyl and a nontoxic, pharmaceutically acceptable water-soluble salt thereof.

Compounds of the formula I wherein $R_3$ is hydrogen can be prepared by reacting mono-alkylamino or di-alkylamino-propionitrile with phosphorus tribromide in the presence of an inert organic solvent or diluent, such as dioxan, the subsequent hydrolysis in water.

Compounds of the formula (I), in which $R_3$ is methyl, can be obtained by reacting β-amino-butyronitrile or N-alkylated-β-amino-butyronitrile with phosphorus tribromide in the presence of an inert organic solvent, such as dioxan, and subsequent hydrolysis of the reaction product in water.

1,3-Di-amino-propane-1,1-diphosphonic acid is obtained by reacting β-amino-propionitrile with phosphorus tribromide, suitably in the presence of an inert organic solvent, and hydrolyzing the reaction product.

In general, the reactions are conducted at slightly elevated temperatures of from the ambient temperature up to about 50° C. Preferably the reaction temperature is about 30° C. The phosphorus tribromide is preferably added to the suspension or solution of the nitrile dropwise, although the reactants can be mixed in any order. The hydrolysis step is preferably conducted by the addition of water to the reaction mixture and, after standing for a time, the hydrolysis mixture is heated for several hours at temperatures of 50° C to 75° C. For working up, the solvent is distilled off and the diphosphonic acid is recovered by crystallization or precipitation with an organic liquid such as acetone or ethanol.

More particularly, the above-described process for the production of the new 1,3-di-amino-alkane-1,1-diphosphonic acid compounds consists essentially of the steps of reacting a nitrile of the formula

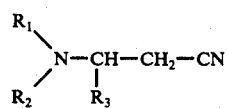

wherein $R_1$ and $R_2$ are members selected from the group consisting of hydrogen and alkyl having from 1 to 3 carbon atoms and $R_3$ is a member selected from the group consisting of hydrogen and methyl, with at least the stoichiometric amount of phosphorus tribromide under anhydrous conditions in the presence of an inert organic solvent or diluent, subjecting the resulting reaction product to aqueous hydrolysis by the action of water, and recovering said 1,3-di-amino-alkane-1,1-diphosphonic acid compound.

The above-described phosphonic acids may be converted into the corresponding water-soluble salts by complete or partial neutralization with inorganic, organic or quaternary ammonium bases, such as NaOH, KOH, NH$_4$OH, alkali metal carbonates, lower-alkanolamines, such as monoethanolamine, diethanolamine and triethanolamine or tetra-lower-alkylammonium hydroxide. Preferably, the alkanolamines have from 2 to 3 carbon atoms in the alkanols and the alkyl ammonium hydroxides have from 1 to 3 carbon atoms in the alkyls.

The above-mentioned compounds, including their alkali metal, ammonium, lower-alkanolamine or tetra-lower-alkylammonium salts, are good complex-forming substances for alkaline earth metal ions, preferably calcium ions, and therefore find special application for water-softening processes. In such case, it is not necessary to work with stoichiometric amounts. It is also possible to considerably inhibit calcite precipitation by use of less than the stoichiometric amounts.

The compounds are, therefore, also very suitable as agents for preventing corrosion and scale in cooling waters, especially in combination with known additives, as for example, divalent zinc and/or cadmium salts, orthophosphates, chromates or hydrazine hydrate.

What is to be regarded as the stoichiometric amount depending on the compound used, can be easily ascertained by a simple experiment. In general, the complex-forming compounds are used in amounts from 1 mol per 2000 mols of metal ions to six times the stoichiometric amount.

The above-mentioned properties have also enabled the new complex-forming compounds, for example, to be used for the descaling of fabrics on which alkali metal salts have been deposited and for the reduction of the ash fraction in fabrics. They are also suitable for the process of cleaning rigid objects, especially metal or glass. In this case, the compound is used especially as an addition to bottle washing agent compositions.

The complex-forming ability can also be advantageously made use of in systems in which copper ions have an unwanted effect. Examples of these are prevention of the decomposition of percompounds or the stabilization of fats and soaps. Further, the said compounds are suitable as additives to dyebaths for textiles, in order to bind metal ions, which form undesired shades of color in complex form.

Finally, the ability of the novel 1,3-di-amino-alkane-1,1-diphosphonic acid compounds to form complexes may also be used in order to add so-called trace elements to plants. The good complex-forming ability of these compounds is demonstrated in that the known red coloration which is usually observed on addition of thiocyanate to solutions which contain trivalent iron does not occur. Therefore, these properties can also be advantageously used to prevent the deposition of iron compounds, especially iron oxide, on fabrics or when washing bottles. The new compounds may also be used in galvanic baths instead of cyanides.

Finally, the compounds are also suitable as builder salts with complex-forming properties in washing and cleaning agent compositions and may be used in combination with known anionic, cationic or non-ionic surface-active compounds or wetting agents. Further, they may be used in combination with caustic alkalis, alkali metal carbonates, alkali metal silicates, alkali metal phosphates or alakli metal borates.

The phosphonic acids described are also suitable for use in pharmaceutical or cosmetic preparations, which are used in order to treat therapeutically or prophylactically disturbances of calcium or phosphate metabolism, as well as the illnesses connected therewith. These diseases can be divided into two categories:

1. Abnormal depositions of difficulty soluble calcium salts, mostly calcium phosphate, cause bone malformations, pathological hardening of tissues and secretions in organs.

2. The abnormal dissolution of hard tissues causes losses of hard bone substance, which cannot be replaced or only by incompletely crystallized tissue. This dissolution is frequently accompanied by pathologically high calcium and phosphate concentrations in the plasma.

These diseases include: osteoporosis, osteodystrophy, Paget's disease, myositis ossificans, Bechterew's disease, cholelithiasis, nephrolithiasis, urinary calculus, hardening of the arteries (sclerosis), arthritis, bursitis, neuritis, tetany.

In addition to the free 1,3-di-amino-alkane-1,1-diphosphonic acids, their pharmacologically harmless salts, such as the alkali metal salts, for example, sodium or potassium or the ammonium salts or the substituted ammonium salts, such as the lower alkanol ammonium salts like the mono-, di-, or tri-ethanol ammonium salts can be used, for use in pharmaceutical preparations in the treatment of these diseases or for their prophylaxis. Both the partial salts, in which only a part of the acid protons are replaced by other cations, and full salts can be used, but partial salts, which react substantially neutral in aqueous solution (pH 5 to 9) are preferred. Mixtures of the above-mentioned salts can likewise be used.

The dosage range of the 1,3-di-amino-alkane-1,1-diphosphonic acid derivative can be from 0.05 to 500 mg per kg of the animal body weight. The preferred dose is 1 to 50 mg per kg of body weight, and can be administered up to four times daily. The higher doses are necessary for oral application, due to the limited resorption. With longer lasting treatments after initially higher doses, smaller doses are normally needed, in order to maintain the desired effect.

Doses under 0.05 mg per kg of body weight have little effect on the pathological calcification or dissolution of bone substance. Doses above 500 mg/kg of body weight may have toxic side effects in the long run. The 1,3-di-amino-alkane-1,1-diphosphonic acid derivatives can be administered orally and, in hypertonic solution, subcutaneously, intramuscularly or intraperitoneally. The preferred ranges of dosing for these applications (in mg/kg per day) are:

Orally — 1 to 50
Subcutaneously — 1 to 10
Intramuscularly — 0.05 to 10
Intravenously — 0.05 to 2

The substances may be formulated for dispensing in tablets, pills, capsules or solutions for injection. The application may be effected in combination with the hormone calcitonine. For the animals the 1,3-di-amino-alkane-1,1-diphosphonic acid derivatives may also be used in food or as additions to food.

When used in cosmetic preparations the 1,3-diaminoalkane-diphosphonic acid is generally added in the form of its alkali metal salts to the corresponding oral hygiene products and dentrifices, such as toothpastes, mouthwashes, tooth cleaning powders, mouth lozenges, chewing gum, and tooth treatment ointments in amounts of 0.01% to about 5% by weight. Oral hygiene products which are necessarily swallowed, like mouth lozenges and chewing gum, should only contain small amounts of up to about 1% by weight; those that are frequently swallowed by accident should not contain more than about 2.5% by weight. The highest amounts can be incorporated in tooth treatment ointments which are used locally by the dentist for the treatment of acute cases.

The pH value of the oral hygiene products and dentrifices according to the invention can range from 5 to 9. The lower limit should not be set lower for safety reasons, to prevent damage to the tooth enamel in a combination of unfortunate circumstances, despite the great safety in the treatment with 1,3-diaminoalkane-diphosphonic acid. The upper limit results from practical considerations, since it is not possible to produce alkaline products which are satisfactory in aroma and taste.

The suitability of the 1,3-diaminoalkane-diphosphonic acid derivatives to be used according to the invention for the therapeutic and prophylactic treatment of tartar results from its capacity of inhibiting even in small amounts crystallization. The precipitation in the presence of 1,3-diaminoalkane-diphosphonic acid, is X-ray amorphous, in contrast to crystalline apatite which is usually formed without this addition.

In mouthwashes, a combination with the aqueous-alcoholic solution of various types of essential oils, emulsifiers, wetting agents, antiseptics, astringents and tonicizing drug extracts, caries-preventing additives, and flavor correctives can be readily used. Hydrogen peroxide-containing mouthwashes, which can also be used to prevent paradontosis, can also be provided with the additive according to the invention.

The toothpastes are generally pasty preparations of water, thickeners, wetting and foaming agents, moisturizers, abrasives, scouring and cleaning agents, aromas, flavor corrective, antiseptics and other valuable oral-cosmetic substances. The cleaning agents and other additives to be used in the toothpastes according to the invention should, as far as possible, be free of soluble calcium in order not to impair the tartar-preventing action of the 1,3-diaminoalkane-diphosphonic acids.

The cleaning agents are, therefore, primarily secondary calcium phosphate, sodium metaphosphate, precipitated silicas, aluminum silicates, calcium pyrophosphate, and finely dispersed synthetic resins, like melamine-urea-formaldehyde resins or poly-lower alkylmethacrylates. The content of cleaning agent in the toothpastes is generally between 25 and 60%. The wetting and foaming agents used are primarily soapfree anionic surface-active compounds, like fatty alcohol sulfates, e.g., sodium lauryl sulfate, monoglyceride sulfates, sodium lauryl sulfoacetate, sarcosides, taurides and other anionic surface-active compounds which do not influence the taste in amounts of 0.5% to 5%. For the production of the binder for the toothpastes, all thickeners that are customary for this purpose can be used, like hydroxyethyl cellulose, sodium carboxymethyl cellulose, tragacanth, carragheen, agar, gum arabic, as well as additional finely dispersed silicas.

The moisturizers are primarily glycerin and sorbitol in amounts of up to about one-third of the total agent. The desired aroma and flavor can be achieved by the addition of essential oils, like peppermint, clover, wintergreen or sassafras oil, as well as sweetening agents, like saccharin, dulcin, dextrose, levulose, etc. In addition, caries-preventing additives, like fluorides or fluorophosphates can be used. The content of the tartar-preventing 1,3-diaminoalkane-diphosphonic acid to be used in the toothpastes according to the invention is between 0.01 and 5%, particularly 1% and 4%, related to the total mass of the toothpaste.

The activity of 1,3-diaminoalkan-1,1-diphosphonic acid or a nontoxic pharmacologically acceptable water-soluble salt of the above mentioned compounds is probably due to an interaction of the phosphonic acid with the crystal surface of the calcium phosphate.

Finally the new 1,3-di-amino-alkane-1,1-diphosphonic acid compounds are also suitable as additives to preparations for the production of $99^m$-Technitium radiodiagnosis. Bone and tissue illnesses can be recognized and localized by radiography. For this purpose the isotope Technitium-$99^m$, which has a half-life period of six hours, has lately been used.

For its production easily handled apparatus is available, from which by elution with isotonic sodium chloride solution the radioactive isotope in the form of $99^m$-Pertechnate may be obtained.

The $99^m$-Pertechnate differs from the earlier used radioactive fluorine or strontium in that in the body it is not specifically bound in the skeleton or in calcareous tumors. For its use it must, therefore, be reduced to a low stage of oxidation and then be stabilized in this oxidation stage with a suitable complex-forming substance. The complex-forming substance must furthermore have a high selectivity for the preferred absorption on the skeleton or on calcareous tumors.

It has been proved that for these purposes, the above described complex-forming 1,3-di-amino-alkane-1,1-diphosphonic acids or their pharmaceutically-unobjectionable, water-soluble salts are specially suitable. In this case the phosphonic acids are used together with a pharmaceutically useful tin (II), chromium II, or iron II salt, where the reducing salts are present in less than the stoichiometric amounts, referred to the phosphonic acid or its water-soluble salts. The simple production of a highly stable product, which is suitable for sale in solid form as tablets or in the form of a solution, contained in an ampoule, is thereby made possible.

The tablets or the contents of an ampoule, after addition to a Pertechnate solution, form a very effective means for the diagnosis of bone tumors, local disturbances of the bone metabolism and tissue tumors with calcereous deposits.

This invention will now be further described by means of the following non-limitative examples.

EXAMPLE 1

3-Dimethylamino-1-amino-propane-1,1-diphosphonic acid (I, $R_1 = R_2 = CH_3$, $R_3 = H$)

0.5 Mol (49 gm) of 3-dimethylaminopropionitrile were reacted with 1 mol (271 gm) of phosphorus tribromide at 30° C in dioxan as diluent. After hydrolysis with 3 mols (54 gm) of water, the reaction mixture was slowly heated from 30° C to 65° C and stirred for a further 3 hours at this temperature. The dioxan was then steam-distilled off and the aqueous phase was filtered over active charcoal until cear. The clear aqueous phase was then treated with acetone. After drying the precipitate in a vacuum drying oven, 3-dimethylamino-1-amino-propane-1,1-diphosphonic acid was obtained as a water-free product in 31% yield.

Calculated: C, 22.90%; H, 6.11%; N, 10.69%; P, 23.66%. Found: C, 22.57; H, 6.02; N, 10.74; P, 23.51.

Melting Point — 244° C to 246° C Molecular weight from pH titration: 261.6 Calculated: 262

3-Diethylamino-1-amino-propane-1,1-diphosphonic acid is obtained in analogous way when 3-diethylaminopropionitrile is used as starting substance.

EXAMPLE 2

3-Monomethylamino-1-amino-propane-1,1-diphosphonic acid (I, $R_1 = CH_3$, $R_2 = R_3 = H$)

1 Mol (271 gm) of phosphorus tribromide was slowly dropped into 0.5 mol (42 mg) of methylaminopropionitrile in 200 ml of dioxan, while the reaction temperature was kept at 30° C. After hydrolysis with 3 mols of water, the reaction mixture was heated for a further 180 minutes at 65° to 70° C. Then the product was diluted with water and steam distilled and the solution was concentrated. Precipitated ammonium bromide was separated and the solution was treated with an acid exchanger. By treating the filtrate with ethanol and reprecipitating from water, 3-monomethylamino-1-amino-propane-1,1-diphosphonic acid was obtained in a pure crystalline form. After drying at 110° C, 26.1 gm (= 21.1% yield) of the diphosphonic acid were obtained.

Calculated: C, 19.35% H, 5.65% N, 11.29% P, 25.00%. Found: C, 19.45 H, 5.61 N, 11.88 P, 24.70.

Melting Point — 247° C Molecular weight from pH titration: 247.6 Calculated: 248.

EXAMPLE 3

1-3-Di-amino-butane-1,1-diphosphonic acid (I, $R_1 = R_2 = H$, $R_3 = CH_3$)

0.25 Mol (21 gm) of β-aminobutyronitrile were added to 100 ml of dioxan and, at 30° C, 0.5 mol (135.5 gm) of phosphorus tribromide was added dropwise. After hydrolysis with 1.5 mols of water, the reaction mixture was heated for a further 3 hours at 65° C. After addition of 100 ml of water the dioxan was driven off by steam distillation. On cooling the acid crystallized from the clear filtrate. The product was dried in a vacuum drying oven at 110° C after it had been cleaned by suspending in water. Yield: 9.1 gm = 14.7% of 1,3-diamino-butane-1,1-diphosphonic acid.

Calculated: C, 19.35%; H, 5.65%; N, 11.29%; P, 25.00%. Found: C, 18.73; H, 5.62; N, 10.56; P, 24.33.

Melting Point — 255° C Molecular weight from pH titration: 245.2 Calculated: 248.

The 3-monoethylamino-1-amino-butane-1,1-di-phosphonic acid was obtained in an analogous way when β-monoethylamino-butyrontirile was used as starting substance.

EXAMPLE 4

1,3-Di-amino-propane-1,1-diphosphonic acid (I, $R_1 = R_2 = R_3 = H$)

0.25 Mol (17.5 gm) of 2-aminopropionitrile were reacted with 0.5 mol (135.5 gm) of phosphorus tribromide at 30° C in 100 ml of dioxan. After hydrolysis with 1.5 mols (27 gm) of water, the reaction mixture was slowly heated from 30° C to 65° C and stirred at this temperature for a further 3 hours. The solvent was then removed by means of steam and the aqueous phase was filtered over active charcoal. The phosphonic acid was precipitated with alcohol from the concentrated filtrate. Based on the starting nitrile, 3.8 gm (= 6.5%) of anhydrous 1,3-di-amino-propane-1,1-diphosphonic acid were obtained.

Calculated: C, 15.38%; H, 5.13%; N, 11.97%; P, 26.50%. Found: C, 15.38; H, 4.83; N, 12.43; P, 26.09.

Melting Point — 256° C Molecular weight from pH titration: 241.9 Calculated: 234.

3-Dipropylamino-1-amino-propane-1,1-diphosphonic acid was obtained in an analogous way when β-dipropylaminopropionitrile was used as starting substance.

EXAMPLE 5

The sequestering properties of the 1,3-diaminoalkane-1,1-diphosphonic acids according to the invention were determined by the known methods of a modified Hampshire test.

1 gm of the sequestering agent was dissolved in 50 ml of $H_2O$, adjusted with NaOH to a pH of 11. 50 ml of a $Ca^{++}$ solution (1470 mg of $CaCl_2 . 2H_2O/1$) were mixed with 100 ml of a sodium carbonate solution (7.15 gm $NaCO_3 . 10H_2O/1$). Then the solution of the sequestering agent was added in drops from a burette until the calcium carbonate precipitate was redissolved. The values found have been reported in the Table. The Table also contains for comparison the values for 1-hydroxy-3-amino-propane-1,1-diphosphonic acid.

TABLE

| Complex-forming Substance | mg $CaCO_3$/gm Acid pH = 11 |
|---|---|
| 1-Hydroxy-3-amino-propane-1,1-diphosphonic acid | 470 |
| 3-Dimethylamino-1-amino-propane-1,1-diphosphonic acid | >2500 |
| 3-Monomethylamino-1-amino-propane-1,1-diphosphonic acid | 1100 |
| 1,3-Diamino-butane,1,1-diphosphonic acid | 910 |
| 1,3-Diamino-propane-1,1-diphosphonic acid | 630 |

Practically identical results were obtained if, instead of the acids, the corresponding sodium, potassium or ammonium salts were employed.

EXAMPLE 6

For the production of a pharmaceutical preparation in the form of a capsule, the known methods of preparation are followed to prepare capsules having a content per capsule as follows:

| | |
|---|---|
| β-dimethylamino-1-amino-propane-1,1-diphosphonic acid | 100 mg |
| Starch | 20 mg |
| Sodium laurylsulfate | 1 mg |

For the preparation of a tablet, the following recipe was utilized per tablet:

| | |
|---|---|
| 3-Monomethylamino-1-amino-propane-1,1-diphosphonic acid | 50 mg |
| Lactose | 100 mg |
| Starch | 35 mg |
| Magnesium stearate | 2 mg |

EXAMPLE 7

Cosmetic Preparations

The following recipes are suitable as a basic formula for toothpastes:

| | | Parts by Weight |
|---|---|---|
| (a) | Glycerin | 60.0 |
| | Water | 13.5 |
| | Sodium carboxymethyl-cellulose | 0.6 |
| | Sodium Zero gel | 20.0 |
| | Sodium laurylsulfate | 2.0 |
| | Essential oils | 1.0 |
| | Sweetening agent | 0.4 |
| | 1,3-Diamino-butene-1,1-diphosphonic acid | 2.5 |

| | | Parts by Weight |
|---|---|---|
| (b) | Glycerin | 30.0 |
| | Water | 18.5 |
| | Sodium carboxymethyl-cellulose | 1.0 |
| | Aluminum hydroxide | 44.0 |
| | Sodium laurylsulfate | 1.0 |
| | Pyrogenic silica | 1.5 |
| | Essential oils | 1.5 |
| | Sweetening agent | 0.5 |
| | 1,3-Diamino-propane-1,1-diphosphonic acid | 2.0 |

Suitable as a basic formulation for mouthwashes is the following recipe:

| | |
|---|---|
| Ethyl alcohol | 19.5 |
| Glycerin | 7.5 |
| Water | 70.0 |
| Essential oils | 0.2 |
| Sodium laurylsulfate | 0.1 |
| Antiseptic (chlorothymol) | 0.1 |
| Sweetening agent | 0.1 |
| 3-Monomethylamino-1-amino-propane-1,1-diphosphonic acid | 2.5 |

By regular use of the mouthwashes and/or toothpastes containing the above-mentioned 1,3-diaminoalkane-1,1-diphosphonic acids, the formation of tartar could be considerably reduced. The formation of hard compact plaque on the teeth was to a great extent prevented.

The preceding specific embodiments are illustrative of the practice of the invention. It is to be understood, however, that other expedients known to those skilled in the art or discussed herein may be employed without departing from the spirit of the invention or the scope of the appended claims.

We claim:

1. A 1,3-di-amino-alkane-1,1-diphosphonic acid compound of the formula

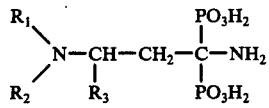

wherein $R_1$ and $R_2$ are members selected from the group consisting of hydrogen and alkyl having from 1 to 3 carbon atoms and $R_3$ is a member selected from the group consisting of hydrogen and methyl and a non-toxic, pharmaceutically-acceptable water-soluble salt thereof.

2. The 1,3-di-amino-alkane-1,1-diphosphonic acid compound of claim 1 wherein $R_3$ is hydrogen.

3. The 1,3-di-amino-alkane-1,1-diphosphonic acid compound of claim 1 wherein $R_3$ is methyl.

4. The 1,3-di-amino-alkane-1,1-diphosphonic acid compound of claim 1 wherein $R_1$ and $R_2$ are methyl and $R_3$ is hydrogen.

5. The 1,3-di-amino-alkane-1,1-diphosphonic acid compound of claim 1 wherein $R_1$ is methyl and $R_2$ and $R_3$ are hydrogen.

6. The 1,3-di-amino-alkane-1,1-diphosphonic acid compound of claim 1 wherein $R_1$ and $R_2$ are hydrogen and $R_3$ is methyl.

7. The 1,3-di-amino-alkane-1,1-diphosphonic acid compound of claim 1 wherein $R_1$, $R_2$ and $R_3$ are hydrogen.